US007192721B1

(12) United States Patent
Esfandiari et al.

(10) Patent No.: US 7,192,721 B1
(45) Date of Patent: Mar. 20, 2007

(54) UNIVERSAL RAPID TEST AND METHOD FOR DETECTION OF TUBERCULOSIS IN MULTIPLE HOST SPECIES

(75) Inventors: Javanbakhsh Esfandiari, Stony Brook, NY (US); Konstantin Lyashchenko, East Setauket, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 0 days.

(21) Appl. No.: 11/222,449

(22) Filed: Sep. 8, 2005

Related U.S. Application Data (63) Continuation-in-part of application No. 11/212,922, filed on Aug. 26, 2005.

(60) Provisional application No. 60/605,304, filed on Aug. 26, 2004.

(51) Int. Cl.
*G01N 33/53* (2006.01)
*G01N 33/354* (2006.01)
*C12Q 1/00* (2006.01)
*A61K 39/395* (2006.01)
*A61K 39/00* (2006.01)

(52) U.S. Cl. ............ 435/7.1; 422/50; 422/56; 422/58; 424/130.1; 424/164.1; 424/168.1; 424/184.1; 435/4; 435/7.32; 436/56; 436/161; 436/162; 436/169

(58) Field of Classification Search ............ 424/130.1, 424/164.1, 168.1, 184.1, 234.1, 248.1; 435/4, 435/7.1, 7.32; 436/56, 161, 162, 164, 169, 436/178; 422/50, 56, 58
See application file for complete search history.

(56) References Cited

OTHER PUBLICATIONS

Zengyi Chang et al. "Mycobacterium tuberculosis 16-kDA Antigen (Hsp16.3) Functions as an Oligomeric Structure in Vitro to Suppress Thermal Aggregation" The Journal of Biological Chemistry, Mar. 22, 1996.

Edward A. Sugden, et al. "Competitive and Indirect Enzyme-Linked Immunosorbent Assays for Mycobacterium bovis Infections Based on MPB70 and Lipoarabinomannan Antigens" Can J Vet Res 1997; 61:8-14.

Morten Haraboe, et al. "Protein G-Based Enzyme-Linked Immunosorbent Assay for Anti-MPB70 Antibodies in Bovine Tuberculosis" Journal of Clinical Microbiology, May 1990.

Colette, J. O'Loan, et al. "Immunoblot Analysis of Humoral Immune Responses to Mycobacterium bovis in Experimentally Infected Cattle: Early Recognition of a 26-Kilodalton Antigen" Clinical and Diagnostic Laboratory Immunology, Sep. 1994, p. 608-611.

M. Amadori, et al. "Antibody Tests for Identification of Mycobacterium bovis-Infected Bovine Herds" Journal of Clinical Microbiology, Feb. 1998.

R. Scott Larsen, et al. "Evaulation of a Multiple-Antigen Enzyme-Linked Immunosorbent Assay for Detection of Mycobacterium Tuberculosis Infection in Captive Elephants" Journal of Zoo And Wildlife Medicine 31(3):291-302, 2000.

Hye Cheong Koo, et al. "New Latex Bead Agglutination Assay for Differential Diagnosis of Cattle Infected with Mycobacterium bovis and Mycobacterium avium subsp. paratuberculosis" Clinical and Diagnostic Laboratory Immunology, Nov. 2004, p. 1070-1074.

J. Carriere, et al. "An appraisal of the Bentonite Flocculation Test in the Detection of Bovine Tuberculosis" Can. J. comp. Med. vol. 37, Oct. 1973.

W.R. Waters, et al. "Antibody Responses in Reindeer (Rangifer tarandus) Infected with Mycobacterium bovis" Clinical and Diagnostic Laboratory Immunology. Jun. 2005.

Rena Greenwald. et al. "Improved serodection of Mycobacterium bovis infection in badgers (Meles meles) using multiantigen test formats" Diagnostic Microbiology and Infectious Disease 46 (2003) 197-203.

Konstantin P. Lyashchenko, et al. "Diversity of Antigen Recognition by Serum Antibodies in Experimental Bovine Tuberculosis" Infection and Immunity, Nov. 1998.

W.R. Waters, et al. "Antigen Recognition by Serum Antibodies in White-Tailed Deer (Odocoileus virginianus) Experimentally Infected with Mycobacterium bovis" Clinical and Diagnostic Laboratory Immunology, Sep. 2004, p. 849-855.

Konstantin Lyashchenko, et al. "Association of Tuberculin-Boosted Antibody Responses with Pathology and Cell-Mediated Immunity in Cattle Vaccinated with Mycobacterium bovis BCG and Infected with M. Bovis" Infection and Immunity, May 2004, p. 2462-2467.

*Primary Examiner*—Rodney P Swartz
(74) *Attorney, Agent, or Firm*—Gordon & Jacobson, PC (57) ABSTRACT

A universal test apparatus for detecting tuberculosis (TB) in any of many different species of non-primate mammals is provided. The universal test apparatus includes a test site having a mycobacterial antigen cocktail comprising ESAT-6/CFP10 and 16 kDa/MPB83 polyfusion antigens, and a tracer having the ESAT-6/CFP10 polyfusion antigen and MPB83 antigen conjugated to latex or colloidal gold. The universal test apparatus is effective across genuses, families and orders of non-primate mammals.

22 Claims, 6 Drawing Sheets

ANTIGEN RECOGNITION BY SERUM ANTIBODIES IN BADGER TB

| ANTIGEN | CULTURE-POSITIVE IN CULLING TRIAL (n=45) | | M. bovis-INFECTED IN BROC 1&2 (n=19) | | TOTAL TB SERA (n=64) | |
|---|---|---|---|---|---|---|
| | NUMBER | % | NUMBER | % | NUMBER | % |
| 16kDa/MPB83 | 25 | 56 | 12 | 63 | 37 | 59 |
| MPB83 | 24 | 53 | 11 | 58 | 35 | 55 |
| MPB70 | 13 | 29 | 3 | 16 | 16 | 25 |
| ESAT-6/CFP10 | 9 | 20 | 6 | 32 | 15 | 23 |
| TBF10 | 9 | 20 | 5 | 26 | 14 | 22 |
| ESAT-6 | 6 | 13 | 5 | 26 | 11 | 17 |
| CFP10 | 8 | 18 | 2 | 11 | 10 | 16 |
| 38kDa | 6 | 13 | 1 | 5 | 7 | 11 |
| MPB59 | 7 | 16 | 0 | 0 | 7 | 11 |
| MPB64 | 3 | 7 | 1 | 5 | 4 | 6 |
| 16kDa | 3 | 7 | 0 | 0 | 3 | 5 |

| FIG.5A |
|--------|
| FIG.5B |

UNIVERSAL RAPID TEST AND METHOD FOR DETECTION OF TUBERCULOSIS IN MULTIPLE HOST SPECIES

RELATED APPLICATIONS

This application is a continuation-in-part of U.S. Ser. No. 11/212,922 entitled "Assay for Detecting Tuberculosis In Nonhuman Primates" filed Aug. 26, 2005 (which claims priority from provisional application 60/605,304 filed Aug. 26, 2004)), the complete disclosure of which is hereby incorporated by reference herein. This application is also related to U.S. Ser. No. 11/172,298 entitled "Dual Path Immunoassay Device" (which claims priority from provisional application 60/680,884 and 60/660,695), the complete disclosure of which is hereby incorporated by reference herein.

BACKGROUND OF THE INVENTION

1. Field of the Invention

This invention relates broadly to apparatus and methods for detecting tuberculosis. More particularly, this invention relates to a single test apparatus which is capable of detecting tuberculosis in multiple animal species.

2. State of the Art

Tuberculosis (TB) is a serious disease caused when bacteria attack the respiratory system. Generally, TB is divided into three categories: human, avian, and bovine. Human TB is rarely transmitted to non-humans, although other primates such as monkeys are susceptible to human TB (*Mycobacterium tuberculosis*). Avian TB (*Mycobacterium avium*) is typically restricted to birds, although pigs and occasionally other animals have been found to be susceptible to avian TB. Bovine TB (*Mycobacterium bovis*), also called cattle TB, is the most infectious across species and is capable of infecting most mammals. Bovine TB is caused by the bacterium *Mycobacterium bovis* which is part of the *Mycobacterium tuberculosis* complex. Bovine TB is spread primarily through the exchange of respiratory secretions between infected and uninfected animals. This transmission is most common when animals are in close contact with each other; i.e., animal density plays a major factor in the transmission of *M. Bovis*. While bacteria released into the air through coughing and sneezing can spread the disease, research also suggests that bovine TB can also be contracted from ingesting contaminated food.

Tuberculosis is a chronic disease in which host animals may show no symptoms of infection. For cattle which are part of the human food supply, the United States has a nationwide surveillance program in place at both State and Federally inspected plants. These inspections are post-mortem inspections which look for indicative lesions on organs, intestines and lymph nodes. Additionally, States requiring testing for import or export may conduct a skin test which is an immune response to tuberculin which is derived from killed TB bacteria. Swelling and irritation around the site of injection of tuberculin would be indicative of a potentially infected animal. Further diagnosis would then be required to confirm.

In addition to TB testing of cattle, TB testing is desirable in zoos. One means for detecting TB is tuberculin skin testing (TST) where mammalian old tuberculin is intradermally injected into the skin of the animal. Following injection, the injection site is checked at 24, 48 and 72 hours for a hypersensitivity-induced induration, the appearance of which indicates previous TB exposure.

TST has several serious shortcomings. A first shortcoming is that the TST lacks sensitivity; i.e., there are many false negatives. False negative tests are known to occur in early or advanced disease states. In advanced states, the absence of delayed hypersensitivity may be attributed to anergy; the absence of sensitivity to substances that would normally elicit an antigenic response. Concomitant severe illness, viral infections, nutritional deficiencies, recent immunizations, may also result in false negative reactions.

A second shortcoming of TST is that TST also lacks specificity; i.e., there are false positives. A major cause of these false positive tests is believed to be cross-reactivity between some of the tuberculin antigens and nonpathogenic species of environmental mycobacteria. False positives are also known to arise from nonspecific inflammatory responses by an uninfected animal to a component of mammalian tuberculin.

A third shortcoming of TST is that the reading of the results in somewhat subjective. For example, the reading scale in the U.S. is different than the reading scale in the U.K. and the reading scale in South Africa. Further, because the mammalian old tuberculin itself varies from unit to unit, results are not uniform. The effect of this shortcoming is that in reading a result, it is standard to have three possibilities—positive, negative, and suspect.

A fourth shortcoming of the TST is that the test is labor intensive in that it requires at least two interactions with the animal; i.e., both an injection and an inspection. It also requires that the animal be available for both interactions, which is not always practical and cost-effective for herds and for wildlife.

Because of all of the shortcomings of TST, current testing protocols mandate multiple testing and quarantine of animal species imported into the United States. If any animal tests positive, all other animals from the same shipment must begin a new period of quarantine. In addition, in the U.S. and some other countries, suspect animals may be subjected to an interferon-gamma test which is specific to the species of animal and which is relatively expensive to carry out. However, the results of the interferon-gamma test are affected by the previous TST test, making the entire TB testing algorithm difficult and undesirably expensive and inaccurate.

Recognizing the shortcomings of TST and the effort and costs associated with preventing TB outbreaks, several entities such as the Center for Disease Control, the NIH, the U.S. Public Health Service, and others have called for the development of a quick and reliable test for nonhuman primate TB. In addition, as suggested above, since various State and Federal agencies require TB testing of cattle, it would be extremely useful and desirable to have quick and reliable TB tests for non-primate mammals. Further, since testing for many different animals is desirable in zoo and wildlife settings, it would be extremely useful and desirable to have a single test which could be utilized for multiple species and which is quick and reliable, rather than having separate tests for each different species.

SUMMARY OF THE INVENTION

It is therefore an object of the invention to provide a rapid TB test for non-primate mammals.

It is another object of the invention to provide a universal test apparatus which can be used to detect TB in any of many different species of non-primate mammals.

It is an additional object of the invention to provide recombinant polyfusion mycobacterial-based antigens that are most frequency recognized in non-primate mammal TB infections.

It is a further object of the invention to design a mixture of selected mycobacterial antigens that are both specific and sensitive to TB infection in non-primate mammals.

It is a further object of the invention to provide test methods utilizing the universal test apparatus of the invention.

In accord with these objects, which will be discussed in detail below, a universal test apparatus for detecting TB in any of many different species of non-primate mammals is provided. According to a first embodiment, the test apparatus includes a lateral flow test device including a sorbent material (e.g., a nitrocellulose strip) defining a horizontal flow path with a sample receiving area, a test area, and preferably a conjugate support area. The lateral flow test device may take the form of a dipstick-type device or a device which includes a housing. Where a housing is utilized, a first opening is provided in the housing for receiving the sample, and a window (open or closed) is provided in the housing for viewing the test area. The test site is provided with an immobilized "cocktail" or mixture of antigens, while the conjugate area is provided with a mixture of antigens bound to a tracer such as latex or colloidal gold which will migrate along the flow path. According to the preferred embodiment of the invention, the test site antigen cocktail includes an ESAT-6/CFP10 fusion and a fusion of MPB83 (also known as MPT83) with ACR1 (alphacrystalline) (also known as 16 kDa) which are printed on the nitrocellulose strip. In one embodiment the conjugate area antigen cocktail includes the ESAT-6/CFP10 fusion and MPB83 antigens which are bound to the tracer. The conjugate area cocktail also preferably includes a purified rabbit IgG which is bound to the tracer and which is used in conjunction with a control area which is preferably located downstream from the test area.

According to another embodiment of the invention, as in previously incorporated U.S. Ser. No. 11/172,298, separate flow paths are provided for the sample and the conjugate. The preferred test site antigen cocktail remains the same as does the conjugate area antigen cocktail. However, a separate flow path is utilized for the sample which is provided to the test apparatus and permitted to migrate to the test site for binding thereto prior to a buffer being provided to cause the tracer to migrate to the test site.

According to yet another embodiment of the invention, a universal test apparatus for detecting TB in any of many different species of non-primate mammals is provided and includes a housing, a first opening in the housing for receiving a buffer solution (in the case of a dry conjugate system) or a conjugate solution (in the case of a liquid conjugate system) containing the tracer as described above with reference to the preferred embodiment, a sorbent material defining a horizontal flow path in the housing, a test line or test site with the antigen cocktail described above with respect to the preferred embodiment, a second opening in the housing directly above the test line or test site for receiving a sample, and a filter located in or adjacently below the second opening and above the test line or test site. Such a system is described in U.S. Ser. No. 11/014,140 entitled "Immunoassay Assay Devices and Use Thereof" filed Dec. 16, 2004, which is hereby incorporated by reference herein in its entirety.

Regardless of the embodiment utilized, the provided universal test apparatus is used by providing body fluid (e.g., whole blood, serum, plasma, diaphragm juice, etc.) of the animal being tested, diluting if and as necessary as is well-known in the art, and applying the body fluid sample to the sample receiving area of the test apparatus. Depending upon the embodiment, the application of the sample is followed by application of a buffer solution to the same or a different receiving area. Where the sample includes TB antibodies (i.e., in cases that the animal was infected by TB), in the standard lateral flow embodiment, the TB antibodies will bind to the antigens bound to the tracer, and the resulting conjugate will migrate to the test site, where the conjugate will be captured by the immobilized test site antigen cocktail, thereby providing a visible line indicating TB infection (a "positive" result). In the other embodiments, the TB antibodies will bind to the antigens bound at the test site, and the conjugate, when reaching the test site. Because of the particular cocktail utilized, the presence of TB antibodies in numerous different non-primate mammals (and possibly all non-primate mammals) will be positively detected with a high specificity and a high sensitivity.

Additional objects and advantages of the invention will become apparent to those skilled in the art upon reference to the detailed description taken in conjunction with the provided figures.

BRIEF DESCRIPTION OF THE DRAWINGS

FIG. 1 is a schematic diagram of a first embodiment of a universal test apparatus of the invention.

FIGS. 2, **2*a* and 2*b* are respectively a schematic diagram, a cross-sectional view taken along line 2A—2A of FIG. 2, and a cross-sectional view taken along line 2B—2B of FIG. 2** of a second embodiment of the invention.

FIGS. 3 and **3*a*** are respectively a schematic diagram and a longitudinal view of a third embodiment of a universal test apparatus of the invention.

FIG. 4 is a chart showing various antigens and their effectiveness in identifying TB in infected badgers.

FIG. 5 is a MAPIA chart showing various antigens and their effectiveness in identifying TB in elephants.

DETAILED DESCRIPTION OF THE PREFERRED EMBODIMENTS

Prior to turning to the Figures, the underlying basis of the invention will be described. In the animal kingdom, there are nineteen orders of placental mammals (subclass eutheria). One of the orders is the primate order, which includes humans, monkeys, apes, etc. The remainder of the orders for purposes hereof are called non-primate orders.

The non-primate orders include:

artiodactyla (even-toed ungulates) including the ruminating families of girafidae (giraffes), cervidae (deer, moose, reindeer, elk), antilocaprida (pronghorn antelope), and bovidae (cattle, bison, yaks, waterbucks, wildebeest, gazelles, springboks, sheep, musk oxen, goats), and the nonruminating familes of suidae (pigs), tayassuidae (peccaries), hippopotamidae (hippopotamuses), and camelidae (camels, llamas);

carnivora (carnivores) such as the unretractable claw superfamily which includes Canidae (wolves, dogs, jackals, foxes), ursidae (bears, giant panda), procyonidae (raccoons, lesser pandas, etc.), and mustelidae (martens, weasels, skunks, otters), and the retractable claw superfamily which includes felidae (cats, lions, cheetahs, leopards), hyaenidae (hyenas) and viverridae (mongooses, civets);

cetacea such as whales and dolphins;

chiroptera such as bats including their two suborders and families;

dermoptera such as the misnamed "flying" lemur;

insectivora (insect-eaters) such as hedgehogs, moles, shrews;

lagomorpha such as rabbits, hares and pikas;

macroscelidea such as elephant shrews;

marsupialia (pouched animals) such as kangaroos and opossums;

monotremata (egg-laying mammals) including spiny ant-eaters and platypuses;

perissodactyla (odd-toed ungulates) such as horses, donkeys, zebras rhinos, tapirs;

pholidota such as the pangolin;

pinnipedian such as seals and walruses;

proboscidea such as elephants, mammoths, mastodonts;

rodentia (rodents) such as the aplodontidae family (mountain beavers), the scuiridae family (chipmunks, squirrels, marmots), the cricetidae family (field mice, lemmings, muskrats, hamsters, gerbils), the muridae family of Old World mice and rats, the heteromyidae family of New World mice, the geomyidae family of gophers, and the dipodidae family of jerboas;

sirenia such as sea cows and manatees;

tubulidentata such as aardvarks;

edentata (also called xenarthra) such as sloths and armadillos; and hyracoidae (hyraxes).

For purposes of the invention, the non-primate mammalian orders of most interest include artiodactyla, marsupialia, perissodactyla, and proboscidea, although the invention is not limited thereto. The invention relates to a universal test which may be used to test TB across multiple non-primate mammalian genuses and preferably across multiple non-primate mammalian subfamilies and families, and even across multiple non-primate mammalian orders.

Also, for purposes of this invention, the phrase "Mycobacterial antigen" is defined to encompass all antigenic epitopes, proteins, protein fragments, and peptides associated with all mycobacteria including, but not limited to *Mycobacterium tuberculosis*, *Mycobacterium bovis*, *Mycobacterium africanum*, *Mycobacterium microti*, *Mycobacterium caprae*, *Mycobacterium pinnipedii*, and *Mycobacterium kansasii*.

In addition, for purposes of this invention, the term "antigen" or "antigenic" is defined herein as an entity capable of eliciting an immune reaction in vivo or in vitro assays or other known techniques.

Further, for purposes of this invention, the term "peptides" which describes chains of amino acids is defined as described in previously incorporated U.S. Ser. No. 11/212, 922 entitled "Assay for Detecting Tuberculosis In Nonhuman Primates" filed Aug. 26, 2005, as is the scope of the term "amino acids".

Further yet, for purposes of this invention, the term "bodily fluid" as used herein, includes, but is not limited to saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, and diaphragm or meat juice (i.e., crushed muscle tissue typically obtainable by freezing and thawing or by pressing).

The mycobacterial antigens of the present invention may be synthesized by chemical or biological methods, such as cell culture, recombinant gene expression, and peptide synthesis. Recombinant techniques include gene amplification from DNA sources using the polymerase chain reaction (PCR), and gene amplification from RNA sources using reverse transcriptase/PCR. Peptides and proteins of interest can be extracted from body fluids by known protein extraction methods, particularly the method described by Novotny, W. F., et al., J. Biol. Chem. 264:18832–18837 (1989).

Peptides or protein fragments comprising mycobacterial antigens can be produced as described above and tested for antigenic activity using techniques and methods known to those skilled in the art. Full length proteins can be cleaved into individual domains or digested using various methods such as, for example, the method described by Enjyoji et al., Biochemistry 34:5725–5735 (1995).

Alternatively, fragments are prepared by digesting the entire protein, or large fragments thereof exhibiting antigenic activity, to remove one amino acid at a time. Each progressively shorter segment is then tested for antigenic activity. Similarly, fragments of various lengths may be synthesized and tested for antigenic activity. By increasing or decreasing the length of a fragment, one skilled in the art may determine the exact number, identity, and sequence of amino acids within the protein that are required for antigenic activity using routine digestion, synthesis, and screening procedures known to those skilled in the art.

As set forth in previously incorporated U.S. Ser. No. 11/212,922 entitled "Assay for Detecting Tuberculosis In Nonhuman Primates" filed Aug. 26, 2005, a Multi-Antigen Print ImmunoAssay (MAPIA) may be used to screen various antigens and antigen hybrids (polyfusions) to identify reactivity of those antigens relative to TB samples. Based on various studies conducted using the antigenic proteins MPB83, MPB70, THF10, ESAT-6, CFP10, 38 kDA, MPB59, MPB64, 16 kDa, and the hybrids (i.e., two-protein molecules) 16 kDa/MPB83, and ESAT-6/CFP10, it was found that a mixture or "cocktail" of the hybrids 16 kDa/MPB83, and ESAT-6/CFP10, or a cocktail of their four component parts could be used effectively to detect TB antibodies across multiple non-primate mammalian genuses, across multiple non-primate mammalian subfamilies and families, and even across multiple non-primate mammalian orders. In addition, it is believed that ESAT-6, CFP10 and MPB83, or the hybrid ESAT-6/CFP10 and MPB83 can be almost as effective as the four component (two hybrid) cocktail in effectively detecting TB antibodies across multiple non-primate mammalian genuses, families and orders.

Figure 1:
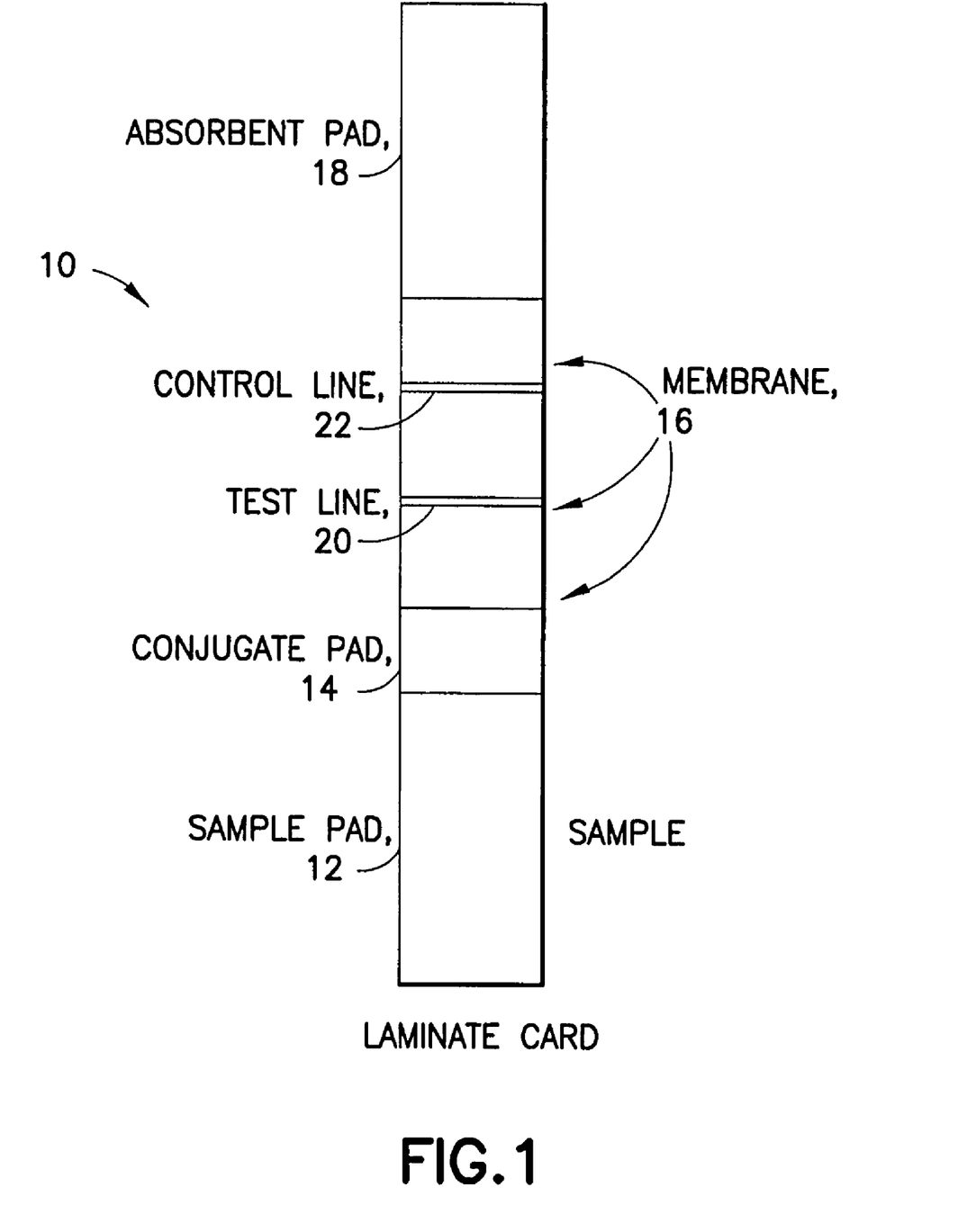

Turning now to FIG. 1, a schematic diagram of a first embodiment of the universal (i.e., cross-genus) TB test apparatus 10 of the invention is seen. The TB test apparatus 10 is effectively a standard lateral flow laminate card format with a sample pad 12, a conjugate pad 14 (in the case of a dry conjugate system), a membrane 16 in fluid contact with the conjugate pad 14, and an absorbent pad 18. Specific mycobacterial antigen mixtures (cocktails) are immobilized onto the membrane 16 at one or more test site locations (typically test lines) 20 of the membrane. According to the preferred embodiment of the invention, the test site antigen cocktail includes an ESAT-6/CFP10 fusion and a fusion of MPB83 with 16 kDa (alphacrystalline) (although the specific antigenic proteins of one or both of the fusions can be substituted for the fusion(s)). As disclosed in the previously incorporated patent applications, any of a number of different membranes are suitable for immobilizing antigens, although nitrocellulose membranes are preferred. Immobilization of the antigen mixtures is possible by any method known in the art, including semiautomated airbrush printing.

In the dry conjugate system the conjugate pad 14 preferably contains a mixture of antigens bound to a tracer such as latex or colloidal gold (or enzyme, fluorescence label) which will migrate along the flow path provided by the membrane. In a preferred embodiment the conjugate area antigen cocktail includes the ESAT-6/CFP10 fusion and MPB83 antigens which are bound to the tracer. The conjugate area cocktail also preferably includes a purified rabbit IgG which is bound to the tracer and which is used in conjunction with a control line or area 22 which is preferably located downstream from the test area. The control line 22 is typically imprinted with goat anti-rabbit IgG which will capture the purified rabbit IgG. The lateral-flow apparatus 10 is typically housed in a housing (not shown) having a hole over the sample pad 12 for receiving a sample, and a window over the test site 20 and control area 22. Alternatively, the lateral-flow apparatus can be arranged as a dip-stick type apparatus. If desired, the sample pad 12 may act as a filter that retains cellular elements of the test sample.

The test apparatus 10 is used by obtaining a test sample from the animal to be tested. The test sample can be any sample capable of containing antibodies to mycobacterial antigens. Preferably, the test sample comprises whole blood or serum. Alternatively, the test sample may comprise any other bodily fluid. As discussed hereinafter, the same universal test apparatus 10 may be used to test the presence of TB in any of multiple non-primate mammalian genuses, and across multiple non-primate mammalian subfamilies and families, and even across multiple non-primate mammalian orders, including (but not limited to) the following animals: cattle, buffalo, white-tailed deer, reindeer, Brockett deer, elk, badger, possum, lion, elephant, gazelle, rhino, giraffe, tapir, llama, alpaca, and jaguar where TB has been detected by the test apparatus.

In the dry conjugate system, the sample is preferably diluted with a buffer and then provided to the test apparatus 10 at the sample pad 12. In the dry conjugate system, the sample migrates to the conjugate pad. Where TB antibodies are present in the sample, the TB antibodies bind to one or more of the antigens bound to the tracer, and the TB antibody-antigen-tracer conjugate migrates down the membrane toward the absorbent pad. When it reaches the test line 20, the antibody-antigen-tracer is captured by the antigen cocktail on the test line, providing an antigen-antibody-antigen arrangement. It is noted that the purified rabbit IgG which is bound to the tracer will bind to the control line/area 22 downstream of the test line, thereby confirming that the sample has indeed reached the test line (in case of a TB "negative" result).

In the wet conjugate system, the sample is mixed with a tracer including colloidal gold or latex particles coated with the antigen cocktail and with the purified rabbit IgG and then optionally diluted with a buffer. The resulting mixture is then applied to the test apparatus 10 at the sample pad 12, where it may be filtered by the pad and then migrates down the membrane (no conjugate pad being provided). If desired additional buffer may be utilized to help migration. Sample buffers compatible with the present invention include, but are not limited to any buffers known in the art such as phosphate buffered saline (PBS), Tris-buffered Saline (TBS) or HEPES buffer that do not cause antibody-antigen dissociation. Where TB antibodies are present in the sample, the TB antibodies bind to one or more of the antigens bound to the tracer, and the TB antibody-antigen-tracer conjugate migrates down the membrane toward the absorbent pad. When it reaches the test line 20, the antibody-antigen-tracer is captured by the antigen cocktail on the test line, providing an antigen-antibody-antigen arrangement. It is noted that the purified rabbit IgG which is bound to the tracer will bind to the control line/area 22 downstream of the test line, thereby confirming that the sample has indeed reached the test line (in case of a TB "negative" result).

Figure 2:
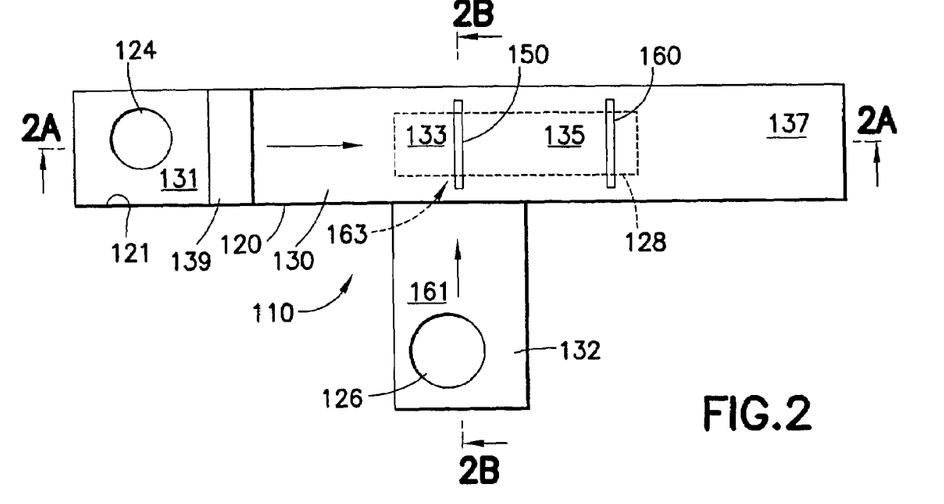
Figure 2A:
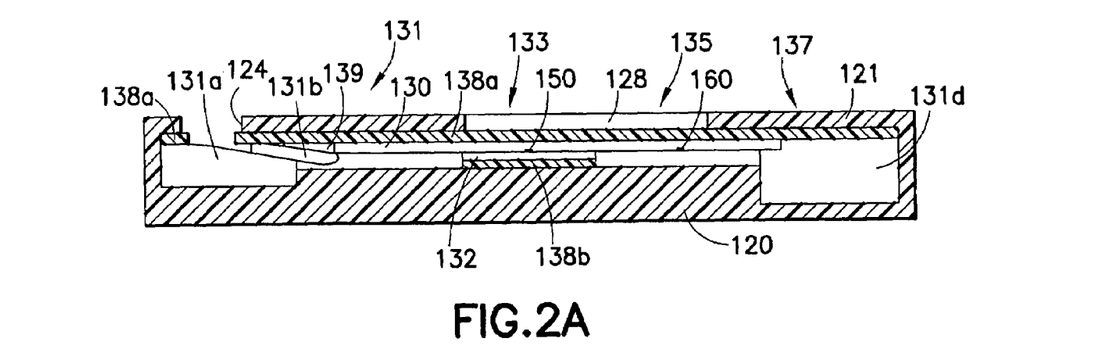
Figure 2B:
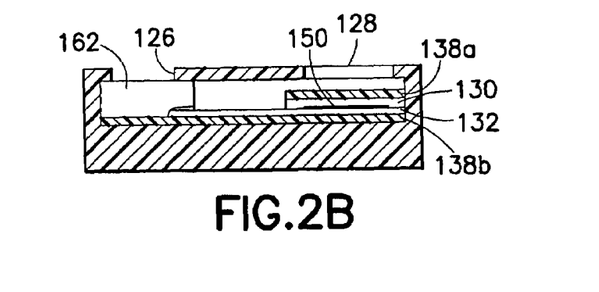

Turning now to FIGS. 2, 2A, and 2B, a schematic diagram of a second embodiment of the universal (i.e., cross-genus) TB test apparatus 110 of the invention is seen. The test cell 110 is provided and includes: a T-shaped housing 120 having a top wall 121 defining first and second holes 124, 126, and a window 128; and first and second sorbent or bibulous materials 130, 132 defining perpendicular horizontal flow paths in the housing. The first sorbent material 130 includes at least two and preferably three or four zones and may be made from a plurality of materials. A first zone 131 (sometimes called a filter zone) is located at the first hole 124 and extends to a second zone 133 (sometimes called a test zone) which is located at the junction of the "T". The first zone 131 preferably includes a filter 131*a*, a pad 131*b* on or in which a conjugate 139 having the antigens cocktail described above with reference to the first embodiment and with attached colored markers (tracer) (and with the rabbit IgG) is deposited and immobilized, and a first portion of a thin membrane or sorbent or bibulous material 130 typically made from nitrocellulose with a plastic backing (not shown). The first zone 131 is adapted to receive a buffer solution, to cause the buffer solution to contact the conjugate, thereby mobilizing the conjugate, and to wick the conjugate-carrying buffer solution to the second zone 133. The second (test) zone 133 includes a second portion of the thin membrane 130 which is preferably printed with a test line 150 having an immobilized antigen cocktail as described above with reference to FIG. 1. The test line 150 may be seen through the window 128 of clear plastic provided in the housing. An optional third zone 135 (sometimes called a control zone) which includes a third portion of the thin membrane 130 may also be printed with a control line 160 typically containing goat anti-rabbit IgG as is well known in the art. Where the third zone 135 is provided, window 128 extends above the control line 160. If desired, an optional fourth zone 137 (sometimes called a reservoir zone) may be provided as a wicking reservoir as is also well known in the art. The fourth zone 137 includes a relatively thicker absorbent paper. Preferably overlying all the zones is a thin, preferably transparent plastic film or card 138*a* having an adhesive which keeps the sorbent materials in place. The card 138 may be cut with an opening at hole 124 so that it does not block liquid access to the hole 124.

The second sorbent material 132 may also be made from a plurality of materials and preferably includes two zones 161, 163. The first zone 161 (sometimes called a filter zone) includes a filter or pad 162 and a first portion of a thin membrane or sorbent or bibulous material 132 typically made from nitrocellulose with a backing (not shown). The first zone 161 is located at the second hole 126 and extends to the second zone 163. The second zone 163 includes a second portion of the thin membrane 132 which is in contact with the second zone 133 of the first sorbent material 130. As is seen in FIGS. 2A and 2B, the first sorbent material 130 overlies the second sorbent material 132 such that the membranes are in contact with each other (as opposed to the backings contacting the membranes or each other), and such that the test line 150 is effectively located between the membranes. Thus, test line 150 could be printed on the second zone 163 of the second sorbent material 132 instead of, or in addition to the second zone 133 of the first sorbent material 130. If desired, a thin plastic film or card 138b having an adhesive which keeps the second sorbent material in place may be utilized.

Where standard-type nitrocellulose strips with a backing are utilized as the first and second membranes, the membranes may have different pore sizes. For example, if membrane 131 (for the conjugate migration) has a 3µ pore size, and membrane 132 (for the sample migration) has a 15µ pore size, sample applied to membrane 132 will tend to migrate and stay in the sample membrane 132 and will tend not to migrate into the conjugate membrane 131.

The universal test apparatus of FIG. 2 is preferably utilized as follows. First, a sample (not shown) from a non-primate mammal possibly containing TB antibodies (or antigens) is provided to the second opening or hole 126 and allowed to migrate through the second sorbent material 132 to its second zone 163 which is contact with the second zone 133 of the first sorbent material 130. Optionally, after providing the sample to hole 126, a preferably measured amount of liquid such as a buffer solution may be added to hole 126 to help in the migration of the sample. Regardless, the sample reaches the test line 150 which is printed atop the second zone 133 of the first sorbent material or infused therein. After a desired amount of time, by which time the antibodies (or antigens) in the sample (if present) will have had an opportunity to bind to the antigens (or antibodies) immobilized at the test line 150, a preferably measured amount of liquid such as a buffer solution (not shown) is added to the first opening 124. After another period of time, sufficient to permit the conjugate to migrate to the test site 150 (and control site 160 if provided), the test site 150 (and control site 160 if provided) is inspected via window 128) in order to determine whether the sample is "positive" or not. Typically, a "positive" test indicating the presence of the antibody (or antigen) in the sample is obtained when both the test site 150 and the control site 160 show lines of color. A "negative" test indicating the lack of the presence of the antibody (or antigen) in the sample is obtained when only the control site 160 shows a line of color.

Figure 3:
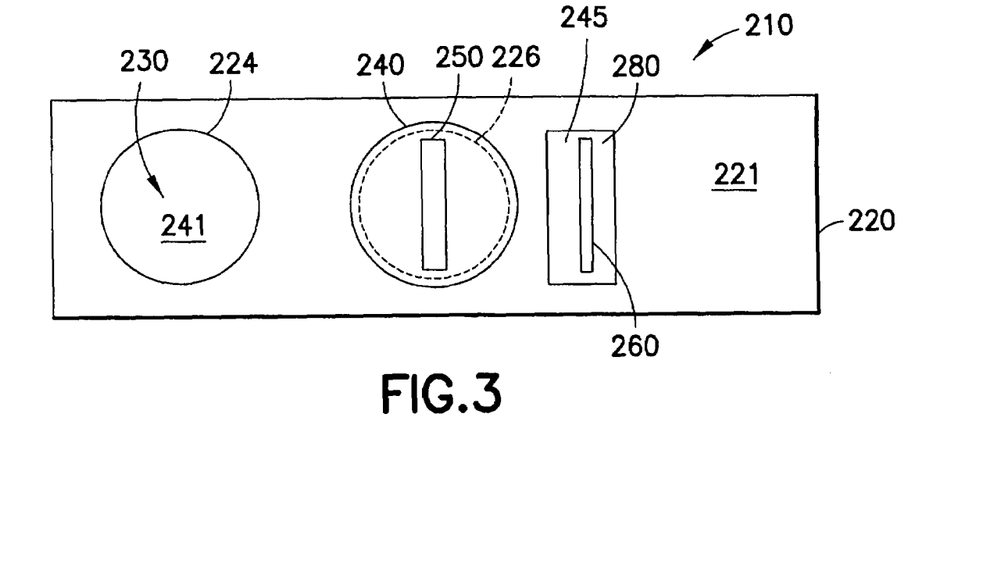
Figure 3A:
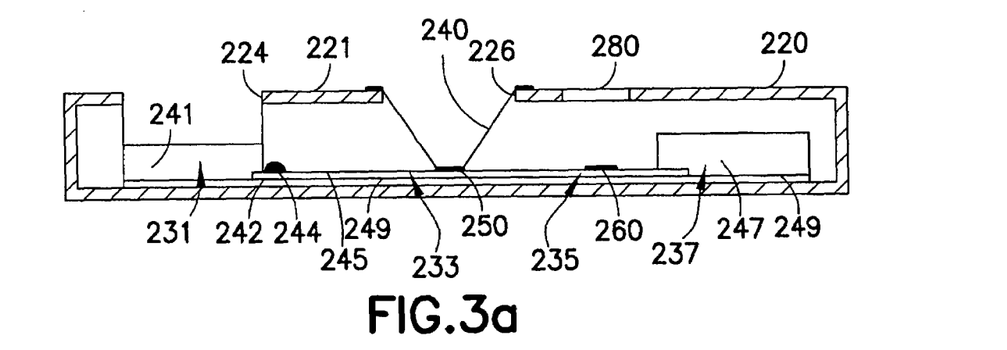

A third embodiment of the universal TB test is seen in FIGS. 3 and 3a, where an immunoassay device test cell 210 is provided and includes a housing 220 having a top wall 221 defining first and second holes 224, 226, a sorbent or bibulous material 230 defining a horizontal flow path in the housing, and a filter 240 located in the second hole 226. The sorbent material includes at least two and preferably three or four zones and may be made from a plurality of materials. A first zone 231 (sometimes called a filter zone) is located at the first hole 224 and extends to a second zone 233 (sometimes called a test zone) which is located under the second hole 226. The first zone 231 preferably includes a filter 241, a pad 242 on or in which a conjugate 244 having the antigen cocktail described above with reference to FIG. 1 with attached colored markers (tracer) is deposited and immobilized, and a thin membrane 245 typically made from nitrocellulose. The first zone 231 is adapted to receive a buffer solution, to cause the buffer solution to contact the conjugate 244, thereby mobilizing the conjugate, and to wick the conjugate-carrying buffer solution to the second zone 233. The second (test) zone 233 is preferably printed with a test line 250 having the immobilized antigen cocktail described above with reference to FIG. 1. on the membrane 245. An optional third zone 235 (sometimes called a control zone) may also be printed with a control line 260 typically containing goat anti-rabbit IgG as is well known in the art. Where the third zone 235 is provided, a window 280 of clear plastic is preferably provided in the housing 220 above the control line 260. If desired, an optional fourth zone 237 (sometimes called a reservoir zone) may be provided as a wicking reservoir as is also well known in the art. The fourth zone 237 includes a relatively thicker absorbent paper 247. Preferably underlying all four zones is a thin plastic film 249 having an adhesive which keeps the sorbent materials in place.

As seen best in FIG. 3*a*, the filter 240 is located directly above the test line 250 in the second zone 233. The filter is preferably an absorbent pad/filter which is coated with plastic except at its bottom area, and which is removably assembled through the second hole 226. In a preferred embodiment of the invention, the filter has a wide circular mouth (coated with plastic) into which the test sample is provided, and is shaped as a funnel which narrows down in one axis only so that a cross-section through the non-coated bottom of the funnel is essentially rectangular in shape and is substantially the same size as the test line 250.

The universal immunoassay of FIGS. 3 and 3*a* is preferably utilized as follows. First, a sample (not shown) from a non-primate mammal, possibly containing TB antibodies is provided to the filter 240 via the second opening or hole 226. Because the filter is coated with plastic on its top portion, the sample is directed to the bottom rectangularly-shaped portion where it is filtered. After a desired amount of time, by which time the antibodies in the sample (if present) will have had an opportunity to bind to the antigens of the antigen cocktail immobilized at the test line 250, a preferably measured amount of liquid such as a buffer solution (not shown) is added to the first opening 224. After another period of time, sufficient to permit the conjugate to migrate to the test site 250 (and control site 260 if provided), the filter 240 is removed, and the test site 250 (and control site 260 if provided) is inspected through hole 226 (and window 280) in order to determine whether the sample is "positive" or not. Typically, a "positive" test indicating the presence of the antibody in the sample is obtained when both the test site 250 and the control site 260 show lines of color. A "negative" test indicating the lack of the presence of the TB antibody in the sample is obtained when only the control site 260 shows a line of color.

EXAMPLE 1

Selection of Antigens

Mycobacterial antigens of the present invention were selected using Multi Antigen Print ImmunoAssay (MAPIA) with respect to badgers. Briefly, antigens were immobilized on a nitrocellulose membrane at a protein concentration of 0.05 mg/ml by using a semiautomated airbrush printing device. The membrane was cut perpendicular to the antigen bands into 4-mm-wide strips. The strips were blocked for 1 hour with 1% nonfat skim milk in PBS, pH 7.2, with 0.05% Tween 20 and then incubated for 1 hour with serum samples of test badgers diluted 1:50 in blocking solution. After being washed, the strips were incubated for 1 hour with horseradish peroxidase-conjugated antibadger IgG monoclonal antibody diluted 1:500 in blocking solution, followed by another washing step. Bound antibodies were visualized with TMB membrane peroxidase substrate. FIG. 4 shows results of the recognition of the badger serum TB antibodies by various antigens. It will be appreciated from FIG. 4, that the hybrids 16 kDa/MPB83 and ESAT-6/CFP10 were more effective in identifying TB antibodies than their component parts, as the three positives identified by 16 kDa were among the sixteen positives of the MPB83, and the total number of separate positives identified by ESAT-6 and CFP10 was less than the number identified by the ESAT-6/CFP10 hybrid.

EXAMPLE 2

Selection of Antigens

Figure 5:
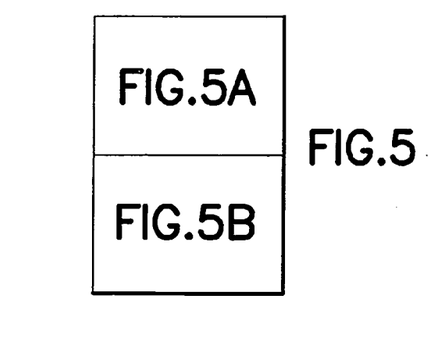
Figure 5A:
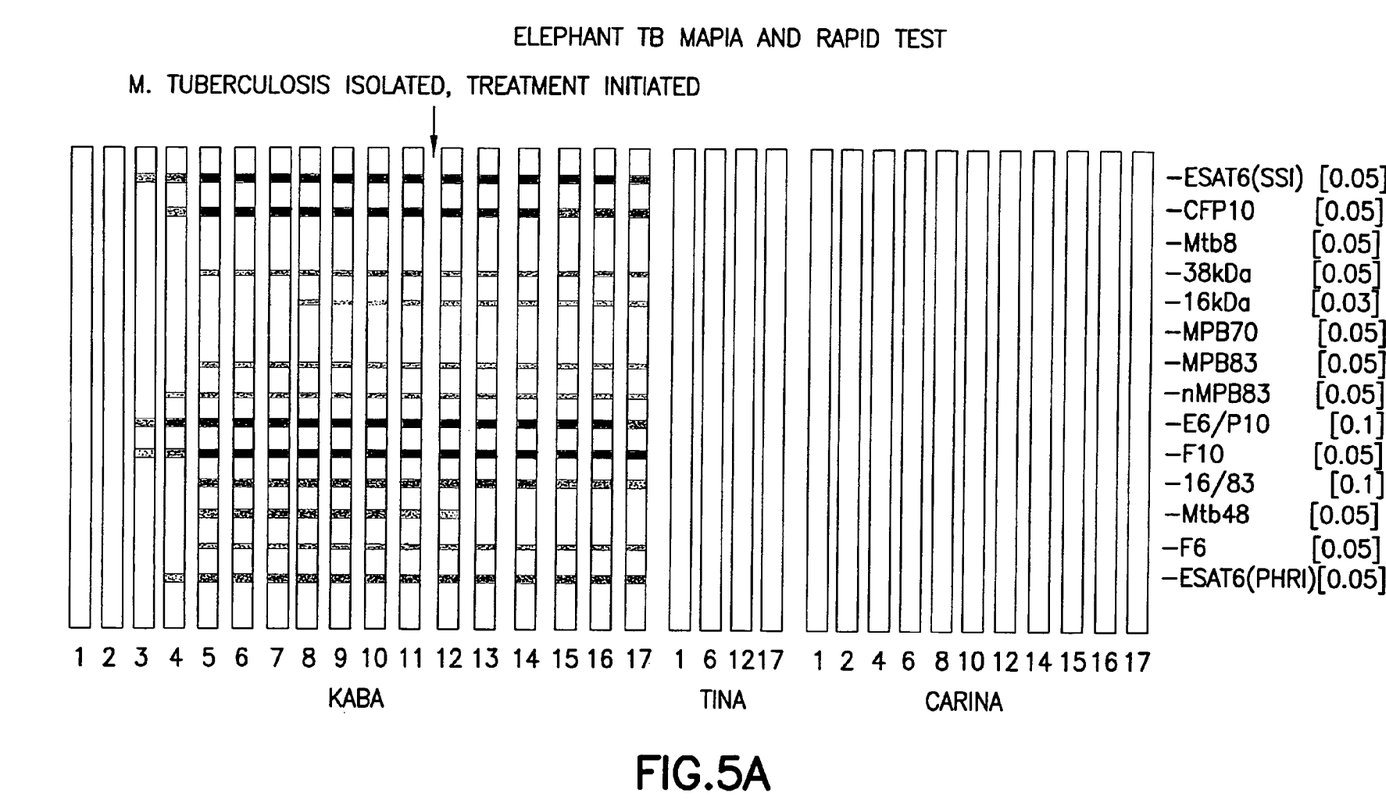
Figure 5B:
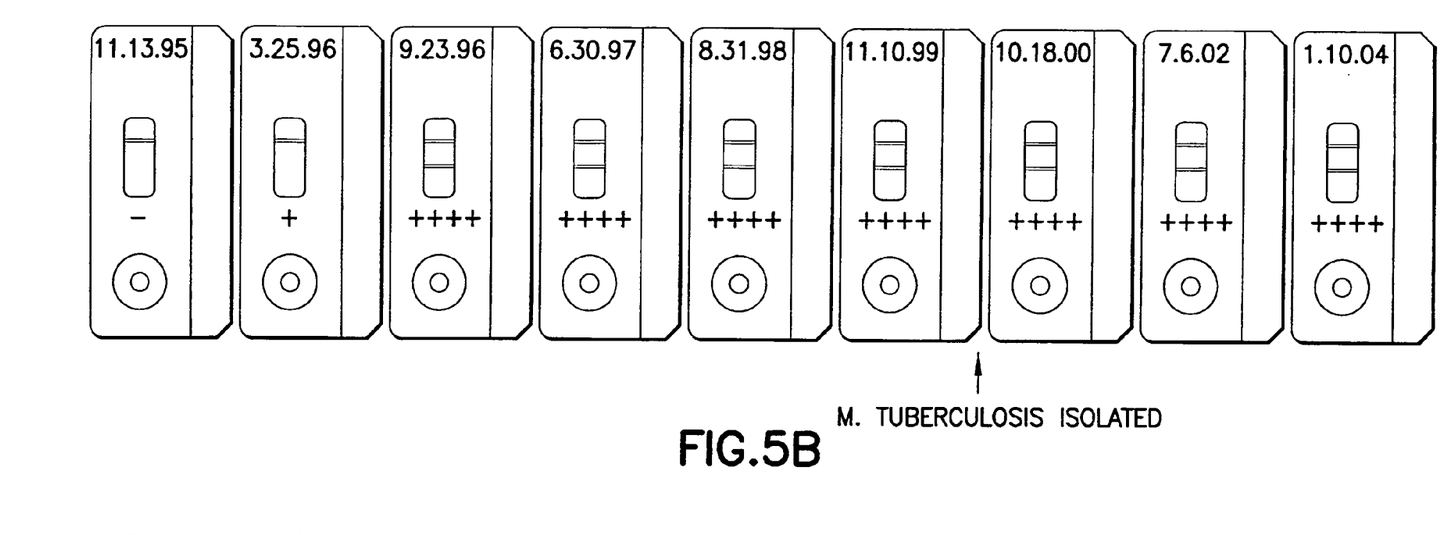

Mycobacterial antigens of the present invention were selected using Multi Antigen Print ImmunoAssay (MAPIA) with respect to elephants. The same procedures as discussed above with reference to EXAMPLE 1 were utilized except that serum samples from ten elephants were applied. FIG. 5 shows results from three of the elephants, with one of the three elephants (Kaba) having TB. In FIG. 5, the ESAT-6/CFP10 hybrid is identified as E6/P10, and the 16 kDa/MPB83 hybrid is identified as 16/83. From FIG. 5 it can be seen (by judging the darknesses of the respective lines) that the 16 kDa/MPB83 is significantly more effective in identifying TB in elephants than either 16 kDa or MPB83 alone.

EXAMPLE 3

Sensitivity and Specificity Tests—Badger

Test apparatus substantially as described above with reference to FIG. 1 were utilized to test results for TB in badgers. The results are set forth in Table 1:

TABLE 1

| Set of Samples | Sensitivity % | Specificity, % |
| --- | --- | --- |
| Experimental *M. bovis* infection (n = 24) | 63 | 96 |
| Culling study-1 (n = 178) | 53 | 95 |
| Culling study-2 (n = 1463) | 50 | 93 |
| Culling study-3 (n = 62) | 60 | NT |
| Excretors (n = 31) | 42 | |
| Super-excretors (n = 31) | 77 | |

From Table 1, it is seen that the apparatus of the invention identified highly infected badgers (super-excretors) at a significantly higher rate than slightly infected badgers (excretors). It will also be appreciated that in all four studies, the apparatus of the invention identified at least 50% of infected badgers with a specificity of at least 93% (no more than 7% false positive).

EXAMPLE 4

Sensitivity and Specificity Tests—White Tailed Deer

Test apparatus substantially as described above with reference to FIG. 1 were utilized to test results for TB in 63 white-tailed deer. The results showed a sensitivity of 72% and a specificity of 93%.

EXAMPLE 5

Sensitivity and Specificity Tests—Reindeer

Test apparatus substantially as described above with reference to FIG. 1 were utilized to test results for TB in fifteen reindeer. The results showed a sensitivity of 91% and a specificity of 93%.

EXAMPLE 6

Sensitivity and Specificity Tests—Elk

Test apparatus substantially as described above with reference to FIG. 1 were utilized to test results for TB in elk. The results showed a sensitivity of 64% and a specificity of 100%.

EXAMPLE 7

Sensitivity and Specificity Tests—Cattle

Test apparatus substantially as described above with reference to FIG. 1 were utilized to test results for TB in cattle. The results are set forth in Table 2:

TABLE 2

| Mycobacterium species | Induced Infection | Natural Infection | Total |
| --- | --- | --- | --- |
| M. bovis | 24/32 | 43/53 | 67/85 |
| M. avium | 0/4 | 2/10 | 2/14 |
| M. paratuberculosis | 0/6 | 2/11 | 2/17 |
| BCG | 1/20 | NA | 1/20 |
| None | 0/26 | 3/43 | 3/69 |

Based on Table 2, it will be appreciated that the sensitivity of the test to *M. bovis* was 79% with a specificity of 93%. Additional tests of 513 cattle yielded a sensitivity of 73% and a specificity of 96%.

EXAMPLE 8

Comparison of Bodily Fluids in White-Tailed Deer

Test apparatus substantially as described above with reference to FIG. 1 were utilized to test results for various different bodily fluids of white-tailed deer. In particular, results from five different fluids in each of four different white-tailed deer were compared. The results are seen in Table 3.

TABLE 3

| Group | Animal # | Serum | Plasma | Whole Blood | Diaphragm Juice | Aqueous Humor |
| --- | --- | --- | --- | --- | --- | --- |
| Control | 603 | − | − | − | − | − |
| M. bovis | 528 | ++ | ++ | ++ | ++ | − |
| M. bovis | 571 | +++ | +++ | +++ | ++ | − |
| M. bovis | 729 | ++ | ++ | + | ++ | − |

From Table 3, it will be appreciated that the results from all bodily fluids are very similar except that positive results could not be obtained from aqueous humor. Thus, aqueous humor is not included within the definition of "bodily fluid" for purposes herein.

Figure 4:
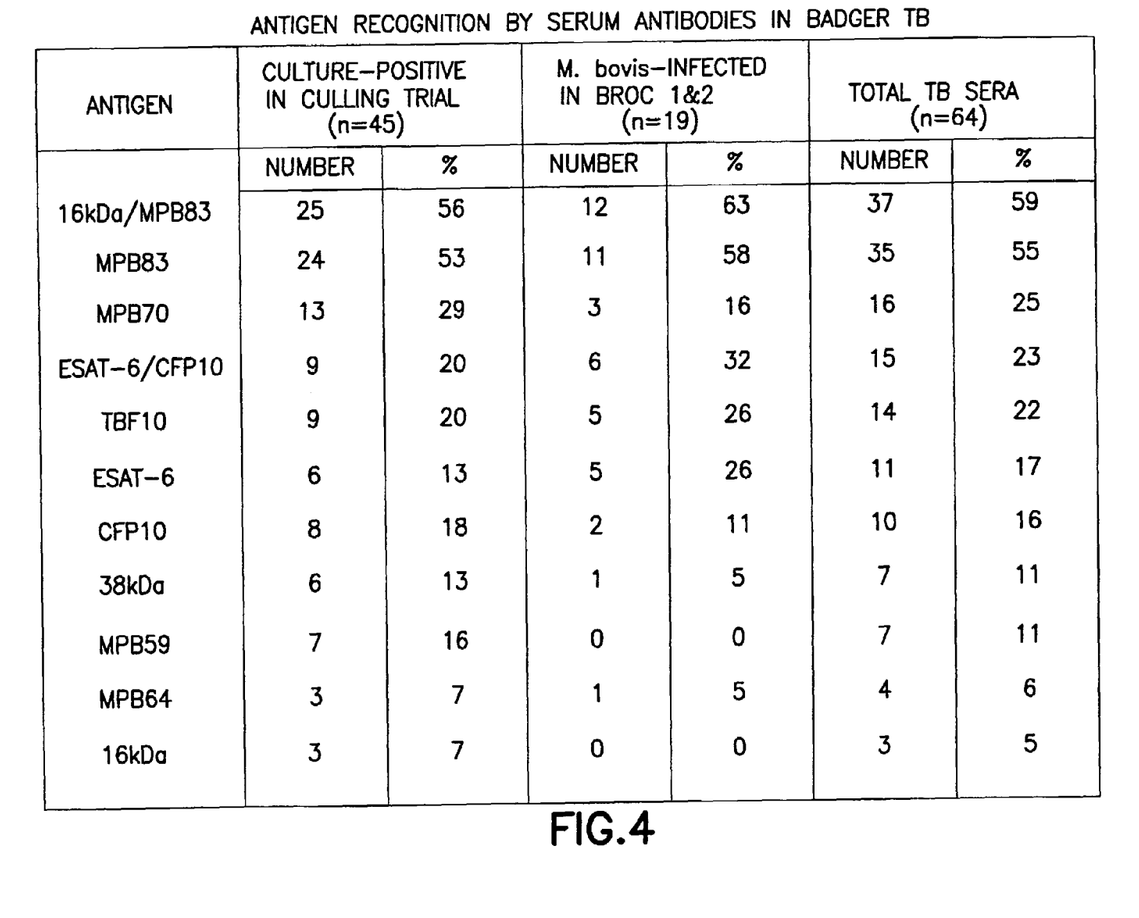

Using the MAPIA test results from badgers (FIG. 4), elephants (FIG. 5) and other animals (not shown), and from additional tests not described, it was determined that the most effective cross-species universal test includes test lines having hybrids (polyfusion proteins) of 16 kDa/MPB83 and ESAT-6/CFP10 attached thereto in substantially equal amounts, and a tracers having a ESAT-6/CFP10 hybrid and MPB83 in substantially equal amounts. Alternatively, the test line could include each of the four antigens separately, or one polyfusion protein and two separate antigens (e.g., 16 kDa/MPB83, ESAT-6 and CFP10). As a further alternative, without losing much sensitivity the test line could include ESAT-6/CFP10 hybrid or its constituents and MPB83 (i.e., not using 16 kDa). In addition, it was determined that the inclusion of additional antigens to the tracer and/or to the test line has a net negative result of reducing at least the specificity of the test device, and in some cases reducing the sensitivity as well due to the typically reduced amount of each antigen available (as more and more antigens are included) to locate on a predetermined area.

Further, in accord with the invention, it is preferred that the test line include approximately 250 nanograms of each fusion antigen, although these amounts can each vary from 150 to 400 nanograms and even less or more, and the conjugate include 50 nanograms each of the fusion ESAT-6/CFP10, and MPB83, although these amounts can each vary from 30 to 80 nanograms and even less or more.

Also, in accord with the invention, essentially identical test devices are to be used with multiple non-primate mammals of at least two different genuses, families, or orders, and preferably with multiple mammals of many different genuses and families. For purposes herein "essentially identical" means that the test devices are manufactured to be the same although they may differ slightly due to manual labor differences, equipment inconsistencies, etc.

There have been described and illustrated herein several embodiments of a universal TB test apparatus for non-primate mammals and a method of their use. While particular embodiments of the invention have been described, it is not intended that the invention be limited thereto, as it is intended that the invention be as broad in scope as the art will allow and that the specification be read likewise. Thus, while particular apparatus have been disclosed, it will be appreciated that other apparatus using the antigen cocktails described may be used as well. Also, while the common names of certain antigens have been utilized, it will be appreciated that identical antigens having different names or equivalent antigens could be utilized, and for purposes herein, the identified antigens are to be understood to include those equivalents. For example and not limitation, for purposes herein, MPB83 should be understood to include MPT83. It will therefore be appreciated by those skilled in the art that yet other modifications could be made to the provided invention without deviating from its spirit and scope as claimed.

What is claimed is:

1. A test apparatus for detecting antibodies to a mycobacterial antigen in non-primate mammals, comprising of a test strip having thereon a mycobacterial antigen cocktail consisting essentially of either (i) ESAT-6, CFP10, and MPB83 antigens or amino acid sequence fragments thereof exhibiting antigenic activity, or (ii) ESAT-6, CFP10, MPB83, and M. tuberculosis 16 kDa antigens or amino acid sequence fragments thereof exhibiting antigenic activity.

2. A test apparatus according to claim 1, wherein:
said ESAT-6 and CFP10 are included as a polyfusion protein ESAT-6/CFP10.

3. A test apparatus according to claim 2, wherein:
said MPB83, and M. tuberculosis 16 kDa are included as a polyfusion protein 16 kDa/MPB83.

4. A test apparatus according to claim 3, wherein:
said ESAT-6/CFP10 and said 16 kDa/MPB83 are included in approximately equal amounts.

5. A test apparatus according to claim 1, further comprising:
a tracer including ESAT-6, CFP10, and MPB83 antigens or amino acid sequence fragments thereof exhibiting antigenic activity.

6. A test apparatus according to claim 5, wherein:
said ESAT-6 and said CFP10 of said tracer are included as a polyfusion protein ESAT-6/CFP10.

7. A test apparatus according to claim 6, wherein:
said polyfusion protein ESAT-6/CFP10 and said antigen MPB83 are included in approximately equal amounts in said tracer.

8. A test apparatus according to claim 5, wherein:
said tracer includes colloidal gold or colored latex.

9. A test apparatus according to claim 8, wherein:
said tracer includes rabbit IgG.

10. A method of testing multiple non-primate mammals for mycobacterial antibodies, comprising:
a) obtaining a corresponding multiple of test devices, each test device comprising a test strip having thereon a mycobacterial antigen cocktail comprising ESAT-6, CFP10, MPB83 antigens or amino acid sequence fragments thereof exhibiting antigenic activity;
b) obtaining bodily fluid from each of said multiple non-primate mammals;
c) applying said bodily fluid of each of said multiple non-primate mammals to a respective corresponding test device; and
d) inspecting said test devices to determine the presence or lack thereof of said mycobacterial antibodies, wherein
said multiple non-primate mammals include non-primate mammals of at least two different genuses.

11. A method according to claim 10, wherein:
said multiple non-primate mammals include non-primate mammals of at least two different families.

12. A method according to claim 11, wherein:
said multiple non-primate mammals include mammals of at least two different orders.

13. A method according to claim 10, wherein:
said multiple non-primate mammals include at least two of cattle, buffalo, white-tailed deer, reindeer, Brockett deer, elk, badger, possum, lion, lynx, wild boar, elephant, gazelle, rhino, giraffe, tapir, llama, alpaca, jaguar, bongo, and kudu.

14. A method according to claim 10, wherein:
said mycobacterial antigen cocktail further comprises M. tuberculosis 16 kDa.

15. A method according to claim 14, wherein:
said mycobacterial antigen cocktail consists essentially of ESAT-6, CFP10, MPB83 and M. tuberculosis 16 kDa antigens or amino acid sequence fragments thereof exhibiting antigenic activity.

16. A method according to claim 14, wherein:
said ESAT-6 and CFP10 are included as a polyfusion protein ESAT-6/CFP10.

17. A method according to claim 16, wherein:
said MPB83 and M. tuberculosis 16 kDa are included as a polyfusion protein 16 kDa/MPB83.

18. a method according to claim 10, wherein:
said plurality of test devices further include a tracer including ESAT-6, CFP10, MPB83 antigens or amino acid sequence fragments thereof exhibiting antigenic activity.

19. A method according to claim 18, wherein:
said ESAT-6 and said CFP10 of said tracer are included as a polyfusion protein ESAT-6/CFP10.

20. A method according to claim 19, wherein:
said polyfusion protein ESAT-6/CFP10 and said MPB83 are included in approximately equal amounts in said tracer.

21. A method according to claim 18, wherein:
said tracer includes colloidal gold or colored latex.

22. A method according to claim 21, wherein:
said tracer includes rabbit IgG.

* * * * *